(12) United States Patent
Lemire

(10) Patent No.: US 8,221,613 B2
(45) Date of Patent: Jul. 17, 2012

(54) DEVICE AND METHOD FOR MEASURING A PLURALITY OF EXHAUST GAS CONSTITUENTS

(75) Inventor: Bertrand Lemire, Schierling (DE)

(73) Assignee: Continental Automotive GmbH, Hannover (DE)

( * ) Notice: Subject to any disclaimer, the term of this patent is extended or adjusted under 35 U.S.C. 154(b) by 967 days.

(21) Appl. No.: 10/557,585

(22) PCT Filed: Mar. 15, 2005

(86) PCT No.: PCT/EP2005/051176
§ 371 (c)(1),
(2), (4) Date: Mar. 6, 2007

(87) PCT Pub. No.: WO2005/095937
PCT Pub. Date: Oct. 13, 2005

(65) Prior Publication Data
US 2008/0011051 A1    Jan. 17, 2008

(30) Foreign Application Priority Data
Apr. 2, 2004  (DE) .......................... 10 2004 016 986

(51) Int. Cl.
*G01N 27/407* (2006.01)

(52) U.S. Cl. ..................... 205/781; 205/784.5; 204/406; 204/425

(58) Field of Classification Search .................. 204/406, 204/424, 425, 427; 205/781, 784.5; 73/23.31, 73/23.32
See application file for complete search history.

(56) References Cited

U.S. PATENT DOCUMENTS

| 5,837,114 | A | * | 11/1998 | Junginger ..................... 204/425 |
| 6,045,673 | A | * | 4/2000 | Kato et al. .................... 204/425 |
| 6,300,753 | B1 | | 10/2001 | Walde et al. |
| 6,637,197 | B1 | | 10/2003 | Stahl |
| 2002/0162755 | A1 | | 11/2002 | Kato et al. |
| 2002/0179458 | A1 | | 12/2002 | Lemire et al. |
| 2004/0045823 | A1 | | 3/2004 | Kawase et al. |

FOREIGN PATENT DOCUMENTS

| DE | 199 07 947 | | 9/2000 |
| DE | 199 223 044 | | 11/2000 |
| DE | 103 39 969 | A1 | 3/2004 |
| EP | 0 816 836 | | 1/1998 |
| EP | 0 999 442 | | 5/2000 |
| WO | WO 03/096005 | | 11/2003 |

* cited by examiner

*Primary Examiner* — Kaj K Olsen
(74) *Attorney, Agent, or Firm* — Lucas & Mercanti, LLP; Klaus P. Stoffel

(57) ABSTRACT

A gas measuring system, having a measurement sensor (1) which records an exhaust gas from an internal combustion engine and has an outer electrode (6), which is exposed to the exhaust gas to be measured, a first measuring cell (4), a second measuring cell (8) that is connected to the first measuring cell (4), and in which a measuring electrode (10) is arranged, and a reference electrode (11) that is exposed to the ambient air. The measuring cells (4, 8) are located in a solid electrolyte (2), and all the electrodes (10, 11) are in contact with the solid electrolyte. A circuit which in a first pump flow ($I_{p0}$) pumps oxygen ions between the first measuring cell (4) and the outer electrode (6), in a second pump flow ($I_{p1}$) pumps oxygen ions between the second measuring cell (8) and the outer electrode (6), and in a third pump flow ($I_{p2}$) pumps oxygen ions between the measuring electrode (10) and the outer electrode (6), and which comprises a control unit (C) which records Nernst voltages between the measuring cells (4, 8) and a reference electrode (11).

10 Claims, 1 Drawing Sheet

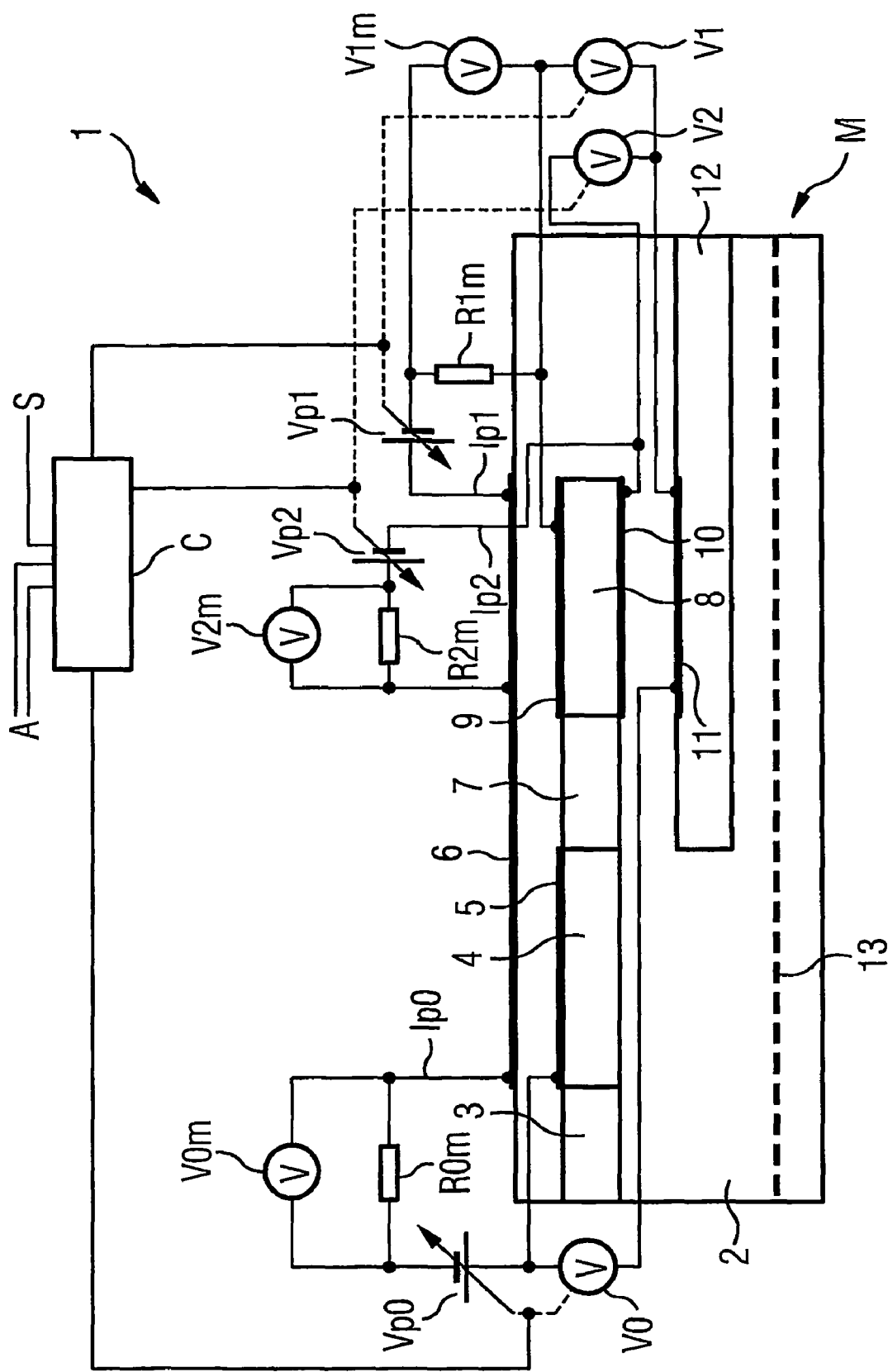

DEVICE AND METHOD FOR MEASURING A PLURALITY OF EXHAUST GAS CONSTITUENTS

This application is a 371 National Stage Entry of application PCT/EP2005/051176 filed on Mar. 15, 2005, which claims priority to application DE 10 2004 016 986.1, filed on Apr. 2, 2004.

FIELD AND BACKGROUND OF THE INVENTION

The invention relates to a gas-measuring system having a measurement sensor which records the exhaust gas from an internal combustion engine and has an outer electrode, which is exposed to the exhaust gas to be measured, a first measuring cell, a second measuring cell, which is connected to the first measuring cell and in which a measuring electrode is arranged, and a reference electrode, which is exposed to the ambient air, the measuring cells being located in a solid electrolyte, and all the electrodes being in contact with the solid electrolyte, a circuit, which in a first pump flow pumps oxygen ions between the first measuring cell and the outer electrode, in a second pump flow pumps oxygen ions between the second measuring cell and the outer electrode and in a third pump flow pumps oxygen ions between the measuring electrode and the outer electrode, and which comprises a control unit, which records Nernst voltages between the measuring cells and a reference electrode and controls the second pump flow to a desired value by evaluating the recorded Nernst voltages. The invention also relates to a method for operating a measurement sensor that records an exhaust gas from an internal combustion engine and has an outer electrode, which is exposed to the exhaust gas to be measured, a first measuring cell, a second measuring cell, which is connected to the first measuring cell and in which a measuring electrode is arranged, and a reference electrode, which is exposed to the ambient air, the measuring cells being located in a solid electrolyte and all the electrodes being in contact with the solid electrolyte, and for operating a circuit, which pumps oxygen ions in a first pump flow between the first measuring cell and the outer electrode, pumps oxygen ions in a second pump flow between the second measuring cell and the outer electrode, and pumps oxygen ions in a third pump flow between the measuring electrode and the outer electrode, Nernst voltages being recorded between the measuring cells and a reference electrode and the second pump flow being controlled to a desired value by evaluating the recorded Nernst voltages.

Systems of this type, with measurement sensor and circuit, are used as standard for measuring the NOx concentration in the exhaust gas from an internal combustion engine, as described for example in EP 0 816 836 A2. The measurement sensor of the system has two measuring cells in a body made from zirconium oxide which conducts oxygen ions. At this sensor, the circuit implements the following measurement concept: in the first measuring cell, which is supplied with the measurement gas via a diffusion barrier, a first oxygen concentration is set by means of a first oxygen ion pump flow, the intention being for there to be as far as possible no decomposition of NOx. In the second measuring cell, which is connected to the first via a further diffusion barrier, the oxygen content is reduced further by means of a second oxygen ion pump flow. To set the oxygen ion pump flows, the circuit taps off a Nernst voltage in the respective measuring cells, reference always being made to an oxygen content to which a reference electrode is exposed, usually that of the ambient air. Furthermore, the second oxygen ion pump flow and the Nernst voltage of the measuring cell are controlled to a desired value.

The decomposition of NOx at a measuring electrode located in the second measuring cell leads to a third oxygen ion pump flow, which is a measure of the NOx concentration. The entire measurement sensor is in this case brought to an elevated temperature, e.g. 750° C., by means of an electrical heater.

The NOx measuring system mentioned is able to record oxides in the exhaust gas. However, it is not sufficiently suitable for other types of gas components or gas parameters. For components of this type, it has hitherto been imperative to use separate sensors. This applies in particular to the field of automotive engineering, where it is known to use separate oxygen or lambda sensors for oxygen measurement in addition to the above-mentioned NOx measuring system. The outlay which is involved in using a plurality of sensors is of course undesirable.

SUMMARY OF THE INVENTION

Therefore, the invention is based on the object of developing the measuring system mentioned in the introduction in such a way that a plurality of gas constituents can be recorded without additional sensor outlay.

According to the invention, this object is achieved by an exhaust-gas measuring system of the type described in the introduction, in which the control unit of the circuit can be switched to a first operating mode and a second operating mode; in the first operating mode, the desired value for the second pump flow is higher than in the second operating mode, and in the first operating mode a measurement signal for an oxide content in the gas is derived from the value of the third pump flow, and in the second operating mode a measurement signal for an oxygen content or lambda value of the exhaust gas is derived from the first pump flow. The object is also achieved by an operating method of the type described in the introduction for operating a measurement sensor which records an exhaust gas, in which a first operating mode and a second operating mode are provided; in the first operating mode, the desired value for the second pump flow is selected to be higher than in the second operating mode, and in the first operating mode a measurement signal for an oxide content in the gas is derived from the value of the third pump flow and in the second operating mode a measurement signal for an oxygen content or lambda value of the exhaust gas is derived from the first pump flow.

According to the invention, therefore, a sensor which is inherently known per se for the measurement of an exhaust gas oxide content (e.g. NOx) is now operated in two different operating modes, so that two exhaust gas constituent parameters are recorded by one measurement sensor by simply switching between the operating modes. In this context, the invention deliberately makes do without simultaneous measurement of the two exhaust gas components. This approach, which at first glance appears disadvantageous, for the first time allows highly accurate measurement of the two components with little outlay. Since it is possible to switch between the operating modes very quickly, quasi-simultaneous measurement is achieved for many applications.

To select the exhaust gas component which is currently measured, the circuit suitably sets the actuation of the measurement sensor, as described for example in EP 0 816 836 A2 or DE 199 07 947 A1.

The invention makes use of the discovery, which has been made for the first time by the inventors, that a measure of the oxygen content or lambda value can be obtained highly accurately in the first measuring cell if the pump flows are set to values which made satisfactory oxide measurement in the second chamber impossible. At the same time, a lean, i.e. low-oxygen gas composition in the first measuring chamber of the measurement sensor is required for sufficiently accurate measurement of oxide concentrations in the second measuring chamber, so that there is no reduction in the first chamber of the oxides which are yet to be recorded in the second chamber. For the oxide measurement, therefore, the gas mixture in the first measuring chamber has not yet chemically reacted fully, so that it still contains nitrogen oxides. An oxygen concentration or lambda measurement in the first measuring chamber would therefore be subject to an avoidably high error under conditions which are optimum for accurate oxide measurement in the second measuring chamber.

The choice according to the invention of the desired values for the second pump flow from the second measuring chamber establish optimum conditions for the measurement of the corresponding exhaust gas component (oxygen or lambda or oxides) in each of the two operating modes. The invention therefore replaces the simultaneous precise measurement of oxygen content or lambda value which has hitherto been the aim in the prior art with a measurement which is separate in terms of time. In this context, in spark-ignition internal combustion engines the lambda value of the exhaust gas will be recorded, and in diesel internal combustion engines the oxygen content will be recorded. By analogy, the oxygen ion pump flows then in each case behave inversely (into the cells in the case of diesel engines, out of the cells in the case of spark-ignition engines).

To measure the oxygen content or lambda value as accurately as possible in the second operating mode, it is expedient for the Nernst voltage to the reference electrode to be set to a defined desired value in the first measuring cell. An optimum point at which maximum measurement accuracy is achieved is reached at a desired value of 450 mV. It is therefore preferable to implement a refinement of the exhaust-gas measuring system in which the control unit, in the second operating mode, controls the Nernst voltage between the first measuring cell and the reference electrodes to a desired value, in particular of 450 mV. For the operating method, analogously, it is provided as an advantageous refinement that in the second operating mode the Nernst voltage between the first measuring cell and the reference electrode is controlled to a desired value, in particular of 450 mV.

As an alternative or in addition, in the exhaust-gas measuring system according to the invention, for accurate oxygen content or lambda measurement, it is possible to provide that the control unit uses the first and second pump flows to carry out a guide control to control the Nernst voltage between the first measuring cell and the reference electrode. The same advantages are achieved for the operating method if a guide control is carried out by means of the first and second pump flows to control the Nernst voltage between the first measuring cell and the reference electrode.

The switching between the operating modes can take place according to a predetermined time pattern. However, if the switching between operating modes is to take place according to other criteria, which do not lead to a fixed time sequence, the measuring system has to indicate precisely what exhaust gas parameter is being measured. This therefore leads to an expedient configuration of the exhaust-gas measuring system in which the circuit emits an output signal which contains a measurement signal for the constituent parameter (oxides or oxygen or lambda) and a part which indicates the operating mode or the constituent parameter measured. In the operating mode according to the invention, these advantages are achieved analogously if an output signal which contains a part indicating the exhaust gas component concentration and a part indicating the operating mode or the exhaust-gas component measured is emitted.

The switching between the operating modes may take place independently in the exhaust-gas measuring system, for example a specific change which is predetermined in terms of time can be carried out. However, in some applications it is advantageous if the switching of the exhaust-gas measuring system has a control input for switching between the first operating mode and the second operating mode.

BRIEF DESCRIPTION OF THE DRAWINGS

The invention is explained in more detail below by way of example with reference to the drawing. The only FIGURE shows a diagrammatic sectional illustration though an NOx measurement sensor with associated circuitry.

DETAILED DESCRIPTION OF THE PREFERRED EMBODIMENT(S)

The NOx measurement sensor M illustrated records two exhaust-gas parameters of the exhaust gas from an internal combustion engine, namely the NOx concentration and the oxygen content (for diesel systems) or the lambda value (for spark-ignition systems). The measurement sensor M, together with a circuit which comprises, inter alia, a control unit C which in the exemplary embodiment is designed as a controller, forms a measuring system 1 which can work in two operating modes. In a first operating mode, the NOx concentration is measured, while in a second operating mode the oxygen content or lambda value of the exhaust gas from the internal combustion engine is measured. The operating modes differ with regard to the electrical variables set at the measurement sensor M by the control unit C.

The measurement sensor M, which comprises a solid electrolyte 2, in the example $ZrO_2$, receives the exhaust gas to be measured, the NOx concentration and/or oxygen content or lambda value of which is to be determined, via a diffusion barrier. The entire measurement sensor M is brought to operating temperature by an electrical heater 13. The exhaust gas diffuses through the diffusion barrier 3 into a first measuring cell 4. The oxygen content or lambda value of the gas in this measuring cell 4 is measured by tapping off a first Nernst voltage $V0$ between a first electrode 5, which is located in the first measuring cell 4, and a reference electrode 11, which is arranged in a reference cell 12. The reference cell 12 is substantially closed off with respect to ambient air, with suitable measures being taken for pressure compensation under inventive fluctuating ambient pressure.

A predetermined oxygen concentration is set in the first measuring cell 4 using a first circuit arrangement. For this purpose, the first Nernst voltage $V0$ is tapped off from a regulator which is realized by the control unit C and provides a driver voltage $Vp0$ which drives a first oxygen ion pump flow $Ip0$ through the solid electrolyte 2 of the measurement sensor M between the first electrode 5 and an outer electrode 6. Therefore, a predetermined oxygen concentration is present in the first measuring cell 4 and is measured by means of the Nernst voltage $V0$ between the electrode 5 and the reference electrode 11. The measurement of the first oxygen ion pump flow $Ip0$ which is required for control is carried out using a measurement resistor $R0m$ and a voltmeter $V0m$. These are realized, for example, by means of an A/D converter with an internal resistance.

The second measuring cell 8 is connected to the first measuring cell 4 via a further diffusion barrier 7. The gas which is present in the first measuring cell 4 diffuses through this diffusion barrier 7 into the second measuring cell 8.

A second circuit arrangement sets a second oxygen concentration in the second measuring cell. For this purpose, a second Nernst voltage V1 is tapped off between a second electrode 9 and the reference electrode 11 and fed to a regulator, which is once again realized in the form of the control unit C and provides a second driver voltage Vp1, by which a second oxygen ion pump flow Ip1 is driven out of the second measuring cell 8 in order to further reduce the oxygen content in the second measuring cell 8. In this case too, a measurement resistor R1m and a voltmeter V1m are used to regulate the second oxygen ion pump flow Ip1.

By means of the second circuit arrangement, the control unit regulates the second oxygen ion pump flow Ip1 in such a way that a predetermined oxygen concentration is set in the second measuring cell 8.

The pump flows mentioned are controlled differently according to operating mode. To enable oxides, e.g. NOx, to be measured in the first operating mode, the predetermined oxygen concentration in the first measuring cell is selected in such a way that NOx is not affected, in particular not broken down, by the operations taking place. The NOx is then pumped into the second measuring cell 8, at a measuring electrode 10 which-may be catalytic in form, from the measuring electrode 10 towards the outer electrode 6 in a third oxygen ion pump flow Ip2. Since the residual oxygen content in the measuring cell 8 in this first operating mode has dropped to such an extent that the third oxygen ion pump flow Ip2 is carried substantially only by oxygen ions which originate from the decomposition of NOx at the measuring electrode 10, the third pump flow Ip2 is a measure of the NOx concentration in the measuring cell 8 and therefore in the exhaust gas to be measured.

The third oxygen ion pump flow Ip2 is determined using a measurement resistor R2m and a voltmeter V2m, and like the previous pump flows is driven by a driver voltage, in this case Vp2, which is predetermined by the control unit C, which taps off a third Nernst voltage V2 between the measuring electrode 10 and the reference electrode 11.

For the first operating mode, the second and third Nernst voltages V1 and V2 and the second pump flow Ip1 are regulated to constant values. This is done by changing the first and third pump flows Ip0 and Ip2. For sufficiently accurate recording of the NOx concentration, the control unit C sets a lean mix in the first measuring chamber 4 of the measurement sensor M, so that the nitrogen oxides cannot be reduced there, with the result that the gas mixture in the first chamber has not yet chemically reacted fully and still contains nitrogen oxides.

Therefore, the following applies to the first operating mode for recording nitrogen oxides: the first pump flow Ip0 is set in such a way that desired values for V1, Ip1 are maintained. The third pump flow Ip2 is set in such a way that a desired value for V2 is maintained.

For the second operating mode, the measuring unit C controls the desired values for the second Nernst voltage V1 and the second pump flow Ip1 in such a way that a different predetermined first Nernst voltage V0 is set in the first measuring chamber 4, preferably a value of 450 mV. The first pump flow Ip0 then serves as a measure of the oxygen content or lambda value of the exhaust gas and is always dependent on the measurement variable, even in particular in linear fashion dependent on the design.

To enable the first pump flow Ip0 to serve as a sufficiently accurate measure of oxygen content or lambda value, it is also possible to carry out a guide control in the first measuring chamber 4, in which case the first Nernst voltage V0 serves as a control signal.

Therefore, the following applies to the second operating mode for recording of the oxygen content or lambda value: the first pump flow Ip0 is set in such a way that desired values for V1, Ip1 are maintained, and therefore V0 indicates stoichiometric conditions, e.g. 450 mV. The third pump flow Ip2 is not required. Or else Ip0-V0 regulation is realized directly (e.g. to 450 mV), as is known from linear lambda sensors.

The control unit C has a two-part output. On the first part of the output is a signal which indicates the operating mode, for example a signal which codes the gas which has been measured. At the second part of the output A, a signal indicating the concentration value is emitted. The operating mode can be set at the control unit C using an input S. As an alternative or in addition, a requirement imposed on the gas-measuring system for measuring an exhaust gas parameter (oxide content or oxygen content or lambda value) can be entered for example by the control unit of an internal combustion engine via the input S. The entry via the input S may be analog or digital in form, and likewise the output A can provide an analog or digital signal.

I claim:

1. A gas-measuring system, comprising:
   a measurement sensor configured to record an exhaust gas from an internal combustion engine, the sensor having an outer electrode exposed to the exhaust gas, a first measuring cell, a second measuring cell that is connected to the first measuring cell, a measuring electrode arranged within the second measuring cell, and a reference electrode exposed to ambient air,
   the first measuring cell and the second measuring cell being located in a solid electrolyte,
   the measuring electrode and the reference electrode being in contact with the solid electrolyte, and
   a circuit operative to provide a first pump flow of oxygen ions between the first measuring cell and the outer electrode, a second pump flow of oxygen ions between the second measuring cell and the outer electrode, and a third pump flow of oxygen ions between the measuring electrode and the outer electrode,
   a control unit operative to record and evaluate Nernst voltages between a first electrode on the first measuring cell, a second electrode on the second measuring cell, the measuring electrode and the reference electrode and the circuit being operative to control the second pump flow to a desired value based on an evaluation of the Nernst voltages recorded,
   wherein the control unit can be switched between a first operating mode and a second operating mode,
   the desired value for the second pump flow being higher in the first operating mode than in the second operating mode,
   the control unit, in the first operating mode, being configured to regulate second and third Nernst voltages and the second pump flow to constant values by changing the first and third pump flows, and to set a lean mixture in the first measuring cell so that nitrogen oxides are not reduced in the first measuring cell, whereby a measurement signal for an oxide content in the exhaust gas is derived from a value of the third pump flow and, in the second operating mode, being configured to control a desired value of the second Nernst voltage and the desired valve of the second pump flow so that a different predetermined first Nernst voltage is set in the first measuring cell, whereby a measurement signal for an oxygen content or a lambda value of the exhaust gas is derived from the first pump flow; and a control input operative to switch between the first operating mode and the second operating mode.

2. The gas-measuring system as claimed in claim 1, wherein the control unit, in the second operating mode, controls the Nernst voltage between the first measuring cell and the reference electrode to a desired value.

3. The gas-measuring system as claimed in claim 2, wherein the control unit uses the first and second pump flows to carry out a guide control in order to control the Nernst voltage between the first measuring cell and the reference electrode.

4. The gas-measuring system as claimed in claim 1, wherein the control unit emits an output signal which contains a part indicating an exhaust-gas component content and a part which indicates the operating mode or the exhaust-gas component measured.

5. The gas-measuring system as claimed in claim 2, wherein the desired value of the Nernst voltage is 450 mV.

6. An operating method for a measurement sensor that records an exhaust gas from a internal combustion engine, the measurement senor comprising an outer electrode, a first measuring cell, a second measuring cell, which is connected to the first measuring cell, a measuring electrode, a reference electrode, a circuit having a first circuit arrangement with a first pump flow, a second circuit arrangement with a second pump flow, a third circuit arrangement with a third pump flow and a control input, the method comprising the following steps:

exposing the reference electrode to ambient air;

arranging the first measuring cell and the second measuring cell in a solid electrolyte;

contacting the measuring electrode and the reference electrode with the solid electrolyte;

pumping oxygen ions in the first pump flow between the first measuring cell and the outer electrode;

pumping oxygen ions in the second pump flow between the second measuring cell and the outer electrode; and pumping pumps oxygen ions in the third pump flow between the measuring electrode and the outer electrode;

recording Nernst voltages between the measuring cells and the reference electrode, controlling the second pump flow to a desired value by evaluating the recorded Nernst voltages;

providing a first operating mode and a second operating mode with the desired value for the second pump flow being higher in the first operating mode than in the second operating mode;

deriving a measurement signal for an oxide content in the exhaust gas from a value of the third pump flow in the first operating mode that includes regulating second and third Nernst voltages and the second pump flow to constant values by changing, the first and third pump flows, and setting a lean mixture in the first measuring cell so that nitrogen oxides are not reduced in the first measuring cell;

deriving a measurement signal for an oxygen content or a lambda value of the exhaust gas from the first pump flow in the second operating mode that includes controlling a desired value of the second Nernst voltage and the desired valve of the second pump flow so that a different predetermined first Nernst voltage is set in the first measuring cell; and switching the control input between the first operating mode and the second operating mode.

7. The method as claimed in claim 6, wherein in the second operating mode the Nernst voltage between the first measuring cell and the reference electrode is controlled to a desired value.

8. The method as claimed in claim 7, further comprising a step wherein a guide control is carried out by means of the first and second pump flows to control the Nernst voltage between the first measuring cell and the reference electrode.

9. The method as claimed in claim 6, further comprising a step of observing an output signal that is emitted, containing a part which indicates the exhaust gas component concentration and a part which indicates the operating mode or the exhaust gas component measured.

10. The gas-measuring system as claimed in claim 7, wherein the desired value of the Nernst voltage is 450 mV.

* * * * *